United States Patent
Rosenblum et al.

(10) Patent No.: US 6,572,740 B2
(45) Date of Patent: Jun. 3, 2003

(54) ELECTROLYTIC CELL

(75) Inventors: Maya Rosenblum, Ashdod (IL); Gilad Lavi, Lezion (IL); Gil Yigal, Gan-Yavne (IL)

(73) Assignee: Elan Pharma International Limited, Shannon (IE)

( * ) Notice: Subject to any disclaimer, the term of this patent is extended or adjusted under 35 U.S.C. 154(b) by 0 days.

(21) Appl. No.: 09/832,179

(22) Filed: Apr. 11, 2001

(65) Prior Publication Data

US 2002/0027068 A1 Mar. 7, 2002

Related U.S. Application Data

(60) Provisional application No. 60/196,907, filed on Apr. 13, 2000.

(51) Int. Cl.[7] .............................. B23H 11/00; C25B 9/00; C25C 7/00; C25D 17/00; C25F 7/00
(52) U.S. Cl. .................. 204/275.1; 204/278; 204/292; 204/293; 252/500; 252/62.2
(58) Field of Search ................ 252/500, 62.2; 604/890.1, 141; 204/271, 275.1, 278, 265, 266, 228.1, 293, 292, 242, 277; 205/615, 622, 630, 104

(56) References Cited

U.S. PATENT DOCUMENTS

| | | | |
|---|---|---|---|
| 5,062,834 A | 11/1991 | Gross et al. | 604/143 |
| 5,090,963 A | 2/1992 | Gross et al. | 604/132 |
| 5,135,499 A | 8/1992 | Tafani et al. | 604/141 |
| 5,186,805 A | 2/1993 | Gross et al. | 204/265 |
| 5,242,406 A | 9/1993 | Gross et al. | 604/132 |
| 5,242,565 A | 9/1993 | Winsel | 204/265 |
| 5,527,288 A * | 6/1996 | Gross et al. | 604/140 |
| 5,567,287 A | 10/1996 | Joshi et al. | 204/265 |
| 5,704,520 A | 1/1998 | Gross | 222/334 |
| 5,814,020 A * | 9/1998 | Gross | 604/141 |
| 5,925,030 A | 7/1999 | Gross et al. | 604/890.1 |
| 6,042,704 A | 3/2000 | Joshi et al. | 204/265 |

FOREIGN PATENT DOCUMENTS

WO 97/10012 3/1997

OTHER PUBLICATIONS

Patent Abstracts of Japan, 04069564, Apr. 3, 1992, ©JPO & JAPIO, 1992.
E. Gileadi, *Electrode Kinetics*, Part 1, 1993, p. 209, VCH Publishers 1993 edition, No month avail.
Cotton et. al., *Advanced Inorganic Chemistry; A Comprehensive Text*, Part 2. 1972, p.370, Interscience Publishers, 1972 edition, No month avail.

* cited by examiner

*Primary Examiner*—Nam Nguyen
*Assistant Examiner*—Wesley A. Nicolas
(74) *Attorney, Agent, or Firm*—Caesar, Rivise, Bernstein, Cohen & Pokotilow, Ltd.

(57) ABSTRACT

Improved electrolytic cells are described. The cells comprise the novel electrolyte $K_2HPO_4$, or a less alkaline phosphate buffer solution, electrodes having a modified composition, or a combination of the new electrolyte and a modified composition electrode. The $K_2HPO_4$ electrolyte, or less alkaline phosphate buffer solution, and modified electrodes can be used in liquid delivery devices which deliver a liquid agent at a constant rate or a controlled variable rate over a period of time.

8 Claims, 12 Drawing Sheets

FIG. 7  Gas Delivery Rates of Electrolytic Cells Having Copper Electrodes, 5.5 M K₂HPO₄ Electrolyte, a Resistance of 10.9 to 11.1 kOhm, at a Temperature of 33°C

ELECTROLYTIC CELL

This application claims benefit to U.S. Provisional Application Ser. No. 60/196,907, filed Apr. 13, 2000.

FIELD OF THE INVENTION

The present invention is directed to an improved electrolytic cell having novel electrolytes and/or novel electrode materials. The electrolytic cell can be used as a gas generator for a drug delivery device.

BACKGROUND OF THE INVENTION

There are many applications requiring the dispensing or delivering of a liquid at a predetermined or precisely controlled rate. One application requiring a particularly precise rate of delivery is a system for administering a drug, such as insulin or morphine. Precise pumps have been devised for this purpose. However, such pumps are expensive to produce and maintain, and are inconvenient to refill with the periodic dosage requirements.

One solution to this problem is to use an electrolytic cell as a gas generator which functions to dispense a liquid from a device. For example, U.S. Pat. No. 5,062,834 ("the '834 patent"), for "Device for Dispensing a Liquid Particularly Useful for Delivering Medicaments at a Predetermined Rate," describes a device for dispensing a liquid at a predetermined rate. The device comprises a container for the liquid to be dispensed and a piston assembly movable within the container and dividing the container into two expandable-contractible chambers. The first chamber contains the liquid to be dispensed and the second chamber contains pressurized gas which functions to dispense the liquid from the first chamber of the container. The second expandable-contractible chamber includes an electrolytic cell having electrodes and an electrolyte. Upon energization of the cell, the electrolyte conducts current between the electrodes, triggering the generation of gas.

The electrolytic cell of the '834 patent comprises a pair of electrodes and an electrolyte capable of generating a gas upon energization of the electrodes. The gas expands the second chamber which results in displacing a piston, thereby forcing the liquid out from the first chamber. Examples of useful electrolytes include saline solution and other polar solutions or gels which generate hydrogen, oxygen, nitrogen or carbon dioxide. A similar device containing an electrolytic cell is described in U.S. Pat. No. 5,242,406 for "Liquid Delivery Device Particularly Useful for Delivering Drugs."

Another example of an electrolytic cell used in a drug delivery device is given in U.S. Pat. No. 5,090,963 for "Electrochemically Driven Metering Medicament Dispenser." This patent describes a liquid material dispenser comprising an electrolytic cell capable of generating a gas when energized by a source of electric current. The liquid material dispenser comprises a rigid housing having a flexible partition forming two compartments. Upon energization by a source of electric current, the electrolytic cell in the first compartment generates a gas, thereby expanding the first compartment of the dispenser. This results in contracting the second compartment containing the liquid material, thereby dispensing the liquid material. The patent teaches that the electrolyte can be an 8% solution of sodium bicarbonate ($NaHCO_3$) in water or a 4% solution of copper sulphate ($CuSO_4$) in water.

Yet another example of a prior art use of an electrolytic cell in a drug delivery device is given in U.S. Pat. No. 5,186,805 ("the 805 patent") for "Electrolytic Dispensing Device." This patent describes a device similar to that the '834 patent. For this particular adaptation of an electrolytic cell, the electrodes are preferably stainless steel nets or screens. The electrolyte can be a water solution of various salts or acids, such as baking soda (sodium bicarbonate), caustic soda, magnesium sulphate, potassium sulphate, sodium sulphate, potassium nitrate, potassium bicarbonate, boric acid, acetic acid, formic acid, or carbonic acid. The '805 patent teaches that particularly good results were obtained using an 8% solution of baking soda (sodium bicarbonate) as an electrolyte.

Finally, a liquid material dispenser, in which the liquid is forced from the dispenser by a gas generated by an electrolytic cell, is described in U.S. Pat. No. 5,704,520. The electrolytic cell contains electrodes and electrolyte. Suitable electrolytes are disclosed to be sodium bicarbonate and potassium acetate.

While these prior art references describe useful electrolytic cells, there remains a need in the art for improved electrolytic cells useful in drug delivery devices. In particular, there is a need for electrolytic cells having a more constant rate of gas production and electrolytic cells having a controlled variable rate of gas production. The present invention satisfies these needs.

SUMMARY OF THE INVENTION

The present invention is directed to an improved electrolytic cell having a new electrolyte and/or a new electrode composition for water electrolysis or other type of electrochemical reaction. The invention also encompasses pretreatment protocols for electrodes which produce a more efficient electrolytic cell. The electrolytic cell is useful as a gas generator in a drug delivery device.

The improved cell allows for miniaturization of the electrolytic cell and any device incorporating such a cell. The novel electrolytic cell is one of the smallest electrolytic cells comprising a liquid electrolyte. The miniaturization or micronization is possible because the cell delivers a large amount of gas volume as compared to the size and quantity of components. The miniaturized electrolytic cell can be used in human applications, such as for administering drugs to be applied either externally or internally. In addition to being useful on a small scale, the electrolytic cell of the invention can be scaled-up and used in commercial manufacturing settings.

In a first embodiment, the improved electrolytic cell exhibits a constant rate of gas production over a prolonged period of time. For this type of cell, the anode must be insoluble in an anodic dissolution process, which is an electrochemical reaction (this is distinguishable from chemical or other types of dissolution); the cathode can be chosen from a wide variety of materials. Steady state production over an extended period of time, as shown below, is highly desirable as such a constant rate produces a constant rate of drug delivery when the electrolytic cell is employed in a drug delivery device.

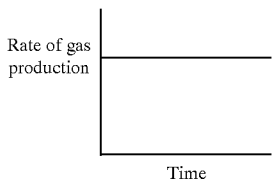

In a second embodiment, the electrolytic cell can be designed to have a controlled variable rate of gas production, as shown below. For this type of cell, the anode is soluble, such as brass or copper. Such a variable rate is desirable for certain types of applications, such as delivering pain medication, in which it is preferred that an initial high delivery rate is followed by a lower constant rate.

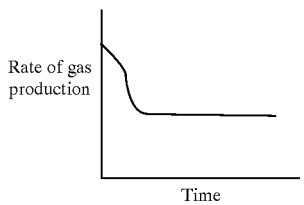

In a third embodiment, the electrolytic cell is designed to have an pulsatile rate of gas production, as shown below. For this type of cell, the anode is insoluble material in an anodic dissolution process, which is an electrochemical reaction (this is distinguishable from chemical or other types of dissolution); the cathode can be chosen from a wide variety of materials. Such an intermittent rate of gas production is useful for certain types of applications, such as for irrigation systems, for the addition of fertility materials to irrigation water, and for administering insulin or hormones to mammals.

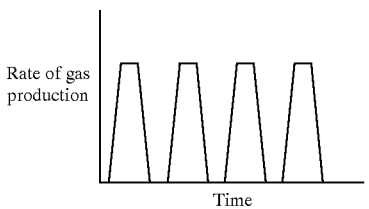

An electrolytic cell of the invention is dramatically superior to prior art cells in that it is simple and cost effective to manufacture, it is composed of materials that are safe and non-toxic, and it can be used in a variety of applications. For example, an electrolytic cell according to the invention can be used in a drug delivery device to administer a steady and controlled amount of drug over an extended period of time. Alternatively, the an electrolytic cell according to the invention can be used to administer a high amount of medication immediately following use, followed by a lower steady rate of administration, or the electrolytic cell can be used to administer a drug at intermittent periods of time.

A. New Electrolyte

The new electrolyte and/or electrode composition are useful in an electrolytic cell comprising the electrolyte and at least two electrodes (anode and cathode) connected to an external source of electrical current, such as a battery, for generating gas. In use, the electrolyte conducts electrical current between the electrodes and, as a result of an electrochemical reaction, gas is generated. The rate of gas production corresponds to the electrical current supplied to the electrolytic cell, and the total amount of gas produced is related to the electrical current supplied to the cell during the time of operation.

The new electrolyte is di-potassium hydrogen phosphate solution, $K_2HPO_4$. Less alkaline phosphate buffer (i.e., $K_2HPO_4+KH_2PO_4$) may also be used as an electrolyte. The preferred pH of the electrolyte is about 8.0 to about 11.0, and the preferred concentration of the electrolyte is from about 1 to about 6 M. For example, the pH of 5.50–5.55 M $K_2HPO_4$ solution is 10.5 to 11.0. The pH of the solution can be reduced to any desired value, such as reducing the pH from 11.0 to 8.0, by adding a proper amount of phosphoric acid of the same molarity. Such a method does not change the concentration of the electrolyte solution.

With the use of a low level of current, i.e., less than about 2 mA, the electrolyte is preferably present at a concentration of about 5.50 to 5.55 M. With the use of a high level of current, i.e., greater than 7 mA, the concentration of the electrolyte is preferably from about 1 M to about 2 M. The new electrolyte is inexpensive, non-toxic, safe, and simple to produce.

An electrochemical gas generator having the new electrolyte delivers gas for an extended period of time. The presence of reactants in suitable amounts and the volume of electrolyte solution are two of the factors which determine the life of the electrolytic cell. Thus, large scale electrolytic cells can operate for years as long as a sufficient quantity of electrolyte solution is present in the cell. The practical limitation of the life span of a micronized or miniaturized cell is the time it takes the electrolyte solution to dry. This is because the electrochemical reaction consumes a relatively negligible amount of water compared with the volume of gas produced. Thus, if water is added to the cell it can be re-used almost indefinitely.

The new electrolyte can be used in any water-electrolysis based electrolytic cell operating at low currents, as well as other types of electrolytic cells operating at high or low currents. The cells can be used, for example, in drug delivery devices, such as those described in U.S. Pat. Nos. 5,242,406; 5,062,834; 5,704,520; 5,090,963; and 5,186,805, which are specifically incorporated by reference.

A drug delivery device incorporating the new electrolyte can be used, for example, in low-cost disposable devices for one-time use and in devices that may be fixed to a band or strap for attachment to the body, e.g., the arm, of the person to receive the medicament dispensed from the device.

B. Electrode Composition

Yet another aspect of the invention is directed to the use of various materials for the electrode. Modification of electrode materials can result in a modification of the rate of gas production, which can thereby control the rate of a substance being delivered. Preferred anode compositions for producing a steady rate or pulsatile rate of gas production are certain noble metals, stainless steel, and nickel. Useful noble metals are, for example, platinum, iridium, rhodium, ruthenium, osmium, and alloys thereof. Gold, or alloys thereof, can also be used, although gold is not preferred because it can cause high overvoltage. Alloys of noble metals for use in anodes of electrolytic cells having steady rate or pulsatile rate of gas production do not contain metals which are soluble in an electrochemical reaction. Stainless steel is preferred as it is inexpensive. Preferred anode compositions for producing an initial high rate of gas production, followed by a lower steady rate of gas production, are brass and copper. Cathode compositions for all three types of gas rate production (steady state, pulsatile, and controlled variable) can be selected from a wide range of materials.

The anode and cathode for all three types of applications can be made of the same or different materials. If the shelf life of the electrolytic cell is to be short, then different materials can be used for the anode and cathode compositions. However, if the shelf life of the electrolytic cell is to be long, then it is preferred that the anode and cathode are made of the same material to avoid potential corrosion during storage.

A device having an electrolytic cell and controlled changes in gas evolution can be used, for example, for pain treatment. Such a device could be used for the delivery of morphine. At initiation, a patient requiring pain treatment requires a high rate of drug delivery. After the initial treatment period, however, the rate of drug delivery must decay. With the use of an electrolytic pump having controlled changes in gas evolution, a drug delivery device can provide a high rate of initial delivery followed by a steady lower rate of delivery. Such a drug delivery device is dramatically superior to prior art delivery devices, as it does not require smart electronics or any other complicated mechanism, and therefore, is simple, efficient, and cost-effective.

C. Treatment Protocol for Electrode Surface

One of the critical parameters of an electrochemical reaction is the initial condition of the electrode surface area. If the electrode surface area is clean and free of an organic or other film or adsorbed species, it is active and electrochemical reactions using the electrode will have high current efficiency.

There are many different methods of pre-treating electrode surfaces, such as mechanical, thermal, chemical, and electrochemical treatments. The method chosen depends upon the intended use of the cell, the electrode design, the nature of the electrolyte, and the cell design. One popular chemical pretreatment method for platinum electrodes uses a "piranha" solution, consisting of a mixture of sulfuric acid and hydrogen peroxide.

For use of the electrolytic cell of the invention in a miniaturized form at low currents, the initial electrode surface is significant as the efficiency of gas delivery is critical. If the electrode surface in such a device was not pretreated, the gas evolution of the device may be unstable (i.e., a non-linear drug delivery curve), the drug delivery may be initially delayed because the current would have to penetrate the electrode surface film, and the repeatability of the results would be poor because the initial electrode surface would not be controlled. This is most significant for drug devices, as regulatory approval of such devices requires that results are repeatable and consistent.

The pretreatment process of the invention comprises pretreating stainless steel, copper, or brass electrodes by washing with ethyl alcohol and rinsing, dipping the electrodes in citric acid and rinsing, followed by activating the electrodes with the electrolyte. A pretreatment process for nickel electrodes is also disclosed.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is directed to an improved electrolytic cell having a new electrolyte and/or a new electrode composition for water electrolysis or other type of electrochemical reaction, and a pre-treatment protocol for electrodes which produces a more efficient electrolytic cell.

The electrolytic cell delivers gas at a stable rate and a relatively high Faradaic current efficiency of, for example, about 70 to about 95%. For electrolytic cells having a steady rate, pulsatile rate, and controlled variable rate of gas production, gas is produced at a rate of from about 0.001 mg/hr up to about 24 ml/hr.

The electrolytic cell of the invention comprises at least two electrodes and the electrolyte of the invention. The two electrodes can be made of the same or different materials, and the electrodes can be made of coated or composite materials. The cathode can be made of a wide variety of metals. The problematic electrode is the anode due to potential corrosion with certain types of metals.

Figure 12:
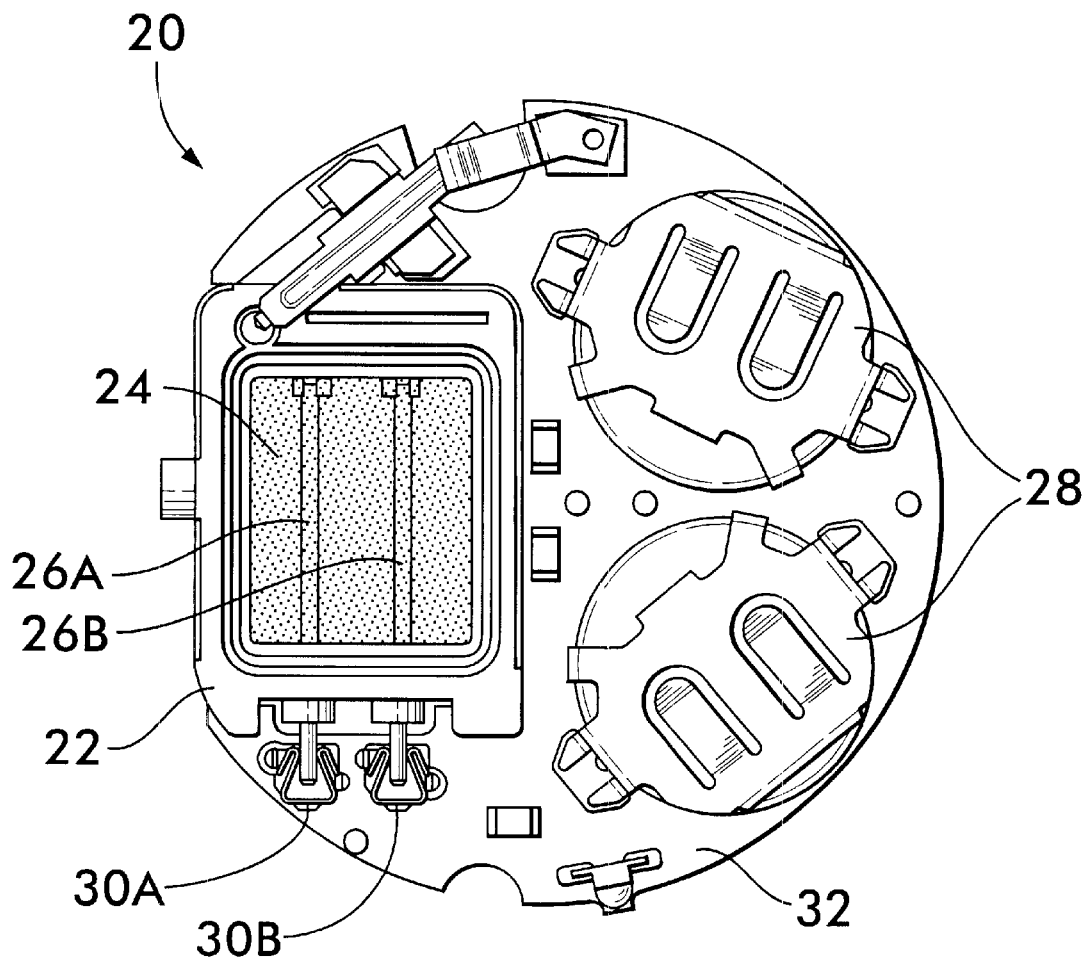
FIG. 12: Is a top plan view of the electrolytic cell of the present invention mounted on the top of a printed circuit board (PCB) with the PCB cover removed and with the cell's upper portion removed.

The electrolytic cell 20 (FIG. 12) of the present invention comprises a housing 22 containing an electrolyte solution 24 having a pair of electrodes 26A (e.g., an anode) and 26B (cathode) that are coupled to a source 28 of electrical current via respective contacts 30A and 30B on a printed circuit board 32. The surface area of each electrode 26A/26B is given by $\pi d l_{eff}$, where d is the diameter of the electrode and $l_{eff}$ is the length of the electrode submerged in the electrolyte solution 24.

A. The New Electrolyte

Di-potassium hydrogen phosphate, $K_2HPO_4$, or less alkaline phosphate buffer electrolyte, is completely safe. Furthermore, in contrast to many prior art electrolytes, the novel electrolyte of the invention does not contain chloride ions. This is significant as an electrolyte containing chloride ions promotes corrosion of the anode if the electrodes are not made of a noble metal.

The new electrolyte is superior to prior art electrolytes as it has a significant buffer capacity that prevents electrode corrosion. Corrosion is one possible side reaction if the anode used in the electrolytic cell is not made from a noble metal. To ensure the stability of gas evolution and high current efficiency, it is desirable to avoid side reactions (except when the electrolytic cell is designed to deliver a controlled variable rate of gas production).

During water electrolysis, there are natural pH changes in electrolyte near the electrodes. The pH near the anode decreases because the electrolyte near the electrode consumes OH⁻ ions due to the electrochemical reaction of oxygen evolution. As a result, anode media becomes more acidic, thereby causing anode corrosion. However, an electrolyte can prevent such pH changes if it has a buffer capacity pH remaining constant near the electrodes. This was demonstrated in U.S. Pat. Nos. 5,186,805 and 5,090,963, in which the only electrolyte tested having a buffer capacity, sodium bicarbonate, showed the best results. However, the novel electrolyte is superior to the prior art $NaHCO_3$ electrolyte in that the buffer capacity of $K_2HPO_4$ is significantly greater than that of $NaHCO_3$.

While sodium bicarbonate has a buffer capacity, there are other properties of the novel electrolyte which are not matched by this prior art electrolyte. The new electrolyte of the invention also prevents corrosion due a build up of a protecting film of phosphates on the electrodes. Specifically, high concentrations of phosphate ions cause polyphosphate creation in the electrolyte solution and on the electrode surface. See Cotton et al., *Advanced Inorganic Chemistry; A Comprehensive Text,* Part 2, page 370 (Interscience Publishers, 1969). This is significant as the phosphate ions protect the surface of both electrodes from contamination and prevent anode corrosion. This superior property of the novel electrolyte of the invention is not found with prior art electrolytes, as it is a characteristic typically only found with phosphates.

Prior art references, such as U.S. Pat. No. 5,186,805, also teach the use of acid electrolytes, which are problematic for water electrolysis. This is because acidic solutions cause corrosion of the anode and high overvoltage of oxygen evolution. High overvoltage of the oxygen evolution electrochemical reaction results in increased cell potential and loss of electrical energy. Thus, alkaline solutions are preferred for water electrolysis.

Yet another benefit of the new electrolyte when it is used at a high concentration, i.e., above about 5.5 M, is that the electrolyte has a high hygroscopicity, which prevents the electrolyte solution from drying during use of the cell, thereby allowing miniaturization of the cell. In contrast, sodium bicarbonate, a common prior art electrolyte, is not hygroscopic and would likely dry with any exposure to the environment. In addition, the amount of dissolved oxygen in the electrolyte is negligible as shown by electrochemical measurements. This is significant as dissolved oxygen can promote anode corrosion. At high concentrations, $K_2HPO_4$ functions to minimize the dissolution of oxygen in the electrolyte.

Moreover, the novel electrolyte is very conductive, with measurements showing conductivity of 112.5 mS/cm at 5.5 M, and 176.5 mS/cm at 2 M.

Not all alkaline solutions produce superior electrolytes for use in a water electrolysis electrolytic cell. A 6 M solution of potassium acetate was tested in an electrolytic cell. This compound is hygroscopic, concentrated, and alkaline. However, potassium acetate is not a buffer. Thus, it was not surprising that with the use of potassium acetate as an electrolyte, the stainless steel anode of the electrolytic cell showed significant corrosion, which increased with electrolysis. As noted above, buffer capacitance is a benefit of the new electrolyte.

B. Limitations on the Design of Electrolytic Cells of the Invention

1. Quantity of Electrolyte

The natural limitation of the reaction time of an electrolytic cell of the invention is the quantity of electrolyte. An electrochemical reaction can be represented schematically by the following equation:

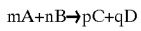

$$mA + nB \rightarrow pC + qD$$

A and B are reactants and C and D are products; m, n, p, and q are stoichiometric coefficients. Consuming the reactants over time leads to an increase in diffusion overvoltage, decrease of reaction rate, possibly pH changes, and in the case of a soluble anode, possible contamination of the electrolyte with sludge. Therefore, it may be necessary to add compounds to commercial electrolytic baths to correct the pH, filter electrolyte, etc. This allows the electrolytic cell to operate for an additional period of time. Replacing the anodes or all of the electrolyte is usually only required after months or years of operation for industrial-size electrolytic cells.

There are two possible time limitations for the length of operation of micronized cells due to the lack of water: electrochemical decomposition of water and drying of the electrolyte. For water electrolysis, the electrochemical decomposition of water is schematically written as follows:

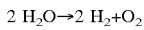

$$2 H_2O \rightarrow 2 H_2 + O_2$$

The amount of water consumed in this reaction is relatively small compared with the volume of gas produced. Theoretically, 36 microliters of water are converted to 73 mililiters of gas at 25° C. Thus, this reaction allows the cell to operate for extended periods of time and it is unlikely to be a limitation upon the operating time period for a cell.

In commercial baths of water electrolysis, water generally has to be added because of evaporation and not because of electrochemical decomposition of water. In a micronized cell having about 0.2 ml or less of electrolyte, drying can be critical to operation of the cell. The cell can't be completely enclosed to avoid drying because a gas outlet must be present. This problem was solved by using highly hygroscopic electrolyte solution, which minimizes the rate of drying of the cell. Operating time of such a cell, without the addition of water, is from about a week to a month. After this time period, the electrochemical reaction become inefficient, although the cell may continue to operate.

Additional limitations on the time of operation of a cell are possible contamination of the electrolyte from the environment and possible contamination with corrosion products or sludge, which can result when soluble anodes are used in the electrochemical cell. For example, brass and copper can be used in an electrochemical cell initially delivering a high rate of gas, followed by a lower steady rate of gas. The steady state delivery period is limited by the existence of the soluble anode material. This time limitation will likely occur after drying of the electrolyte (the most critical time limitation factor for operation of the electrochemical cells of the invention). For example, assuming that 100 $\mu$A is the current fraction responsible for copper anodic dissolution, the amount of copper dissolving per hour is 0.12 mg (Faraday's law). Also assuming that the volume of electrode immersed into solution is about 1.3 g (typical for a miniaturized cell), the time limit because of anodic dissolution is 10,800 hours, which is more than one year.

2. Electrode Surface Area

The primary limitation of minimizing the electrode surface area and, as a result, the size of an electrolytic cell, is the current density, which is the current divided by the electrode surface area. The current density should be kept constant for the same reaction conducted in different types of cells. Thus, the required current density can restrict the minimal electrode surface area required for an electrolytic cell.

For example, assuming that a water electrolysis cell of the invention operates with a 1.5 mA current and a electrode surface area of 0.23 cm². This correlates with a current density of 1.5/0.23=6.5 mA/cm². This current produces about 1 ml/hr of gas (assuming the current efficiency is <100%).

Current density is significant because reaction overvoltage in electrochemistry is dependent upon it. Cell overvoltage is the difference between the cell voltage (with a current flowing) and the open-circuit voltage (ocv) (which is the cell voltage under zero current conditions). The cell overvoltage is the sum of overvoltages of both electrodes plus the IR drop. The overvoltage represents the extra energy needed (an energy loss) to force a slow reaction to proceed at a required rate. Thus, a high overvoltage is undesirable, as it represents a high energy loss.

High reaction overvoltage results in an unstable electrolytic cell, a loss of electrical energy, shorter time of battery discharge, and a decrease of the current. Furthermore, high reaction overvoltage can result in a cell which is more susceptible to contamination of the electrolyte.

When the current density increases, the overvoltage increases. Thus, in designing an electrolytic cell it is desirable to keep the current density relatively low to avoid high overvoltage. This can be done by choosing a electrodes having a sufficient surface area in relationship to the intended voltage to result in a low current density. A lower intended current allows for the use of electrodes having a lower surface area, and conversely, a higher current requires the use of electrodes having a greater surface area, to obtain a desired low current density.

C. Electrode Composition

The anode and cathode for steady state, pulsatile, or a controlled variable rate of gas production can be made of the same or different materials. In general, metals that chemically react with water, such as alkali or alkaline-earth metals, should not be used for electrode materials. In addition, metals having a low standard electrochemical potential, such as zinc, aluminum, tin, etc., should not be used as electrode materials as they will corrode with exposure to the electrolyte. Highly toxic materials, such as lead or cadmium, should not be used as anode materials, although they can be used as cathode materials. Metals or metal alloys, electrodes with modifications made to the surface, or carbon electrodes, operating as each electrode at lower overvoltages are preferred.

For a steady rate or pulsatile rate of gas production, the anode is insoluble, and can be certain noble metals, stainless steel, or pure nickel. Useful noble metals are, for example, gold, platinum, iridium, rhodium, ruthenium, osmium, and alloys thereof. Stainless steel is preferred as it is inexpensive. For steady state or pulsatile delivery, metals capable of dissolving anodically, such as brass, zinc, copper, cobalt, bright nickel, lower grades of steels, silver, etc., should be avoided as anode materials because an insoluble anode is required for water electrolysis. For a controlled variable rate of gas production, the anode is soluble, such as brass or copper.

While the cathode for steady state, pulsatile, and controlled variable rate of gas delivery may be selected from a wide range of materials, certain materials should not be used. Metals capable of absorbing hydrogen, such as palladium and niobium, or reducing to hydrides, such as titanium, zirconium, and tantalum, should not be used as cathodes as they will critically decrease the current efficiency of the cell operation. Tungsten, molybdenum, and titanium should not be used as cathode materials because oxides of these materials can absorb hydrogen, which can decrease the current efficiency of the cell.

Provided below is a chart showing potential anode and cathode materials for water electrolysis electrolytic cells (steady state or pulsatile rate of gas delivery). For a cell having a controlled variable rate of gas delivery, the anode is made of brass or copper (soluble anodes) as described above, and the cathode can be made of the cathode materials given in the following table.

TABLE 1

Potential Electrode Materials for Electrolytic Cells
Having a Steady State or Pulsatile Rate of Gas Delivery
(Water Electrolysis, Electrolyte is $K_2HPO_4$ at 1–6M)

| Number | Anode Material | Comments about Anode | Cathode Material | Comments about Cathode |
|---|---|---|---|---|
| 1 | Stainless steel | | Stainless steel | |
| 2 | Nickel (>99%) | | Nickel | No limitation for Ni kind or its alloys |
| 3 | Platinum | | Platinum including platinum black | Low overvoltage |
| 4 | Iridium | | Iridium | |
| 5 | Rhodium | Low overvoltage | Rhodium | |
| 6 | Ruthenium | High oxidation, Its oxides reduce overvoltage for oxygen evolution. A very good anode | Ruthenium | |
| 7 | Osmium | | Osmium | |
| 8 | Gold | High overvoltage | Gold | High overvoltage |
| 9 | Titanium | High oxidation | | |
| 10 | | | Silver | |
| 11 | | | Cobalt | |
| 12 | | | Copper | |
| 13 | Alloys of mentioned metals | | Alloys of mentioned metals | |
| 14 | Modified electrodes. Examples: (1) ruthenium dioxide on nickel surface (2) Conductive oxides as anode | | Modified electrodes. Example: platinum powder on carbon | |

In general, the anode and cathode for all three types of applications (steady state, pulsatile, and controlled variable rate of gas production) can be made of the same or different materials. If the shelf life of the electrolytic cell is to be short, then different materials can be used for the anode and cathode compositions. However, if the shelf life of the electrolytic cell is to be long, then it is preferred that the anode and cathode are made of the same material to avoid potential corrosion during storage. If both the anode and cathode are made of a noble metal or noble metal alloy (gold and all metals from the platinum group), then the anode and cathode can be made of different materials, regardless of the intended shelf life of the cell. This is because these materials will not corrode during storage.

If the electrodes are made from noble metals (cases 3–8 in the Table), then there are more possibilities for the choice of electrolyte. Noble metals do not dissolve anodically, so the requirements for the electrolyte may be reduced: i.e., it is not required that the electrolyte be a buffer and the electrolyte may have a neutral, acidic, or alkaline pH. The electrolyte in the cell must be hygroscopic and safe and it must contain compounds suitable for evolution of safe gases during electrochemical performance. Several examples of such compounds are:

(1) Aluminum salts—sulfates or nitrate, or potassium alum: $KAl(SO_4)_2$. These salts are very hygroscopic and potassium alum is extremely inexpensive. The pH is slightly acidic. The electrochemical reaction is electrolysis of water.

(2) Hydrosulfates of alkaline metals ($KHSO_4$ or $NaHSO_4$). The pH is acidic and the electrochemical reaction is electrolysis of water; and (3) Acetates, formates, or propionates of alkaline metals. The pH is alkaline. The electrochemical reactions are: (a) electrolysis of water; and (b) gas $CO_2$ evolution. This means that: (i) on the anode there is oxygen evolution and $CO_2$ evolution (Kolbe reaction) (E. Gileadi, *Electrode Kinetics*, Part 1, p. 209 (VCH publishers, 1993)) and (ii) on the cathode there is hydrogen evolution. All of the gases are safe.

D. Use of the New Electrolyte in Different Types of Electrolytic Cells

1. Use of the New Electrolyte in Cells Having Different Levels of Current

The new electrolyte can be used in electrolytic cells having varying levels of current. For example, the $K_2HPO_4$ electrolyte can be used in an electrolytic cell having a high level of current, i.e., above about 7 milliAmpers. With this type of cell, a relatively low concentration of electrolyte should be used, i.e., less than about 2 M.

In a first test, an electrolyte solution of about 5.50 M to about 5.55 M solution of $K_2HPO_4$ was used in the high current cell. A high current results in a high rate of gas production. Use of such a high concentration electrolyte in a high current electrolytic cell required an enlarged electrode surface sufficient for performance at high current. However, it was discovered that such a high concentration electrolyte produced a slow coalescence of creating gas bubbles, forming a solution that resembled an emulsion. The high viscosity of the electrolyte solution prevented the transfer of gas bubbles out of the cell, and resulted in a significant increase in the cell potential at a constant current, without reaching a plateau. This means a high diffusion overvoltage on both electrodes and an increase of the resistance of the solution, producing a high IR drop. An IR drop is a loss of potential caused by current and resistance of the solution. As the IR grows, the loss of energy increases. Thus, given the level of the current for this electrolytic cell, the resulting gas delivery was too slow.

A relatively low concentration $K_2HPO_4$ electrolyte, i.e., an about 1 M to about 2 M solution of $K_2HPO_4$, is preferably used in an electrolytic cell having a high level of current. For example, a 2 M solution of $K_2HPO_4$ used in an electrolytic cell operating at a high current lacked any coalescence problems. Thus, a lower concentration of the electrolyte allows operation of an electrolytic cell at a higher current.

At low concentrations, the $K_2HPO_4$ electrolyte is extremely conductive, with a conductivity of 176.5 mS/cm at 2 M. This is important when operating an electrolytic cell at a high current, as this is when IR drop becomes significant. Moreover, the lower concentration $K_2HPO_4$ electrolyte is even more conductive than the high concentration $K_2HPO_4$ electrolyte: at 25° C. and a 2 M solution, the conductivity is 176.5 mS/cm, while at the same temperature a 5.5 M solution is 112.5 mS/cm. The difference in conductivity is likely caused by a more complete dissociation of ions for the lower concentration $K_2HPO_4$ electrolyte. The lower concentration $K_2HPO_4$ electrolyte is also hygroscopic, although its hygroscopicity is lower than the more concentrated form of the $K_2HPO_4$ electrolyte.

Figure 6:
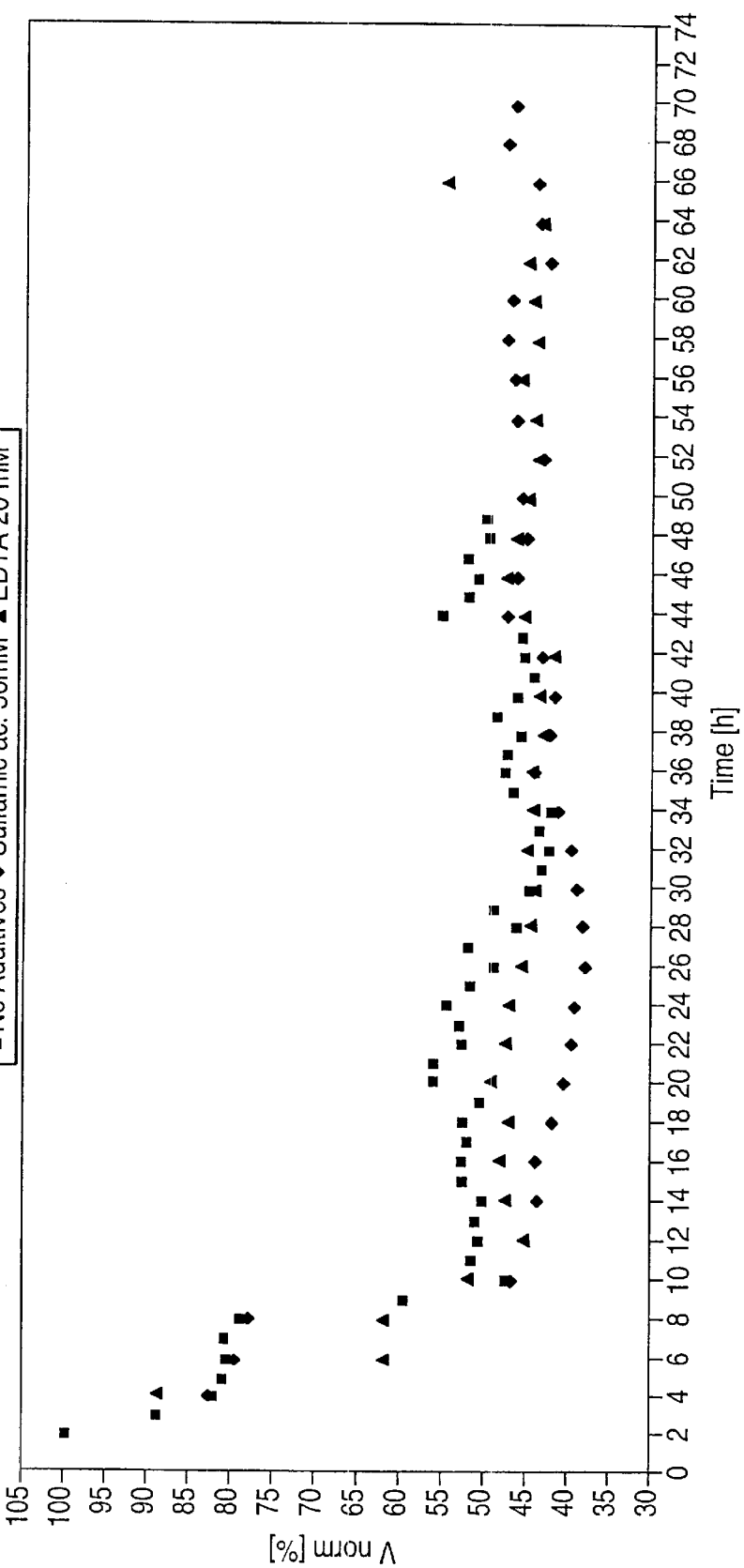
FIG. 6: Shows a graphical comparison of a normalized reaction rate for gas for three different electrolyte cells having brass electrodes and electrolyte compositions of: (1) 5.5 M. $K_2HPO_4$; (2) 5.5 M. $K_2HPO_4$ and EDTA; and (3) 5.5 M. $K_2HPO_4$ and sulfamic acid.
Figure 9:
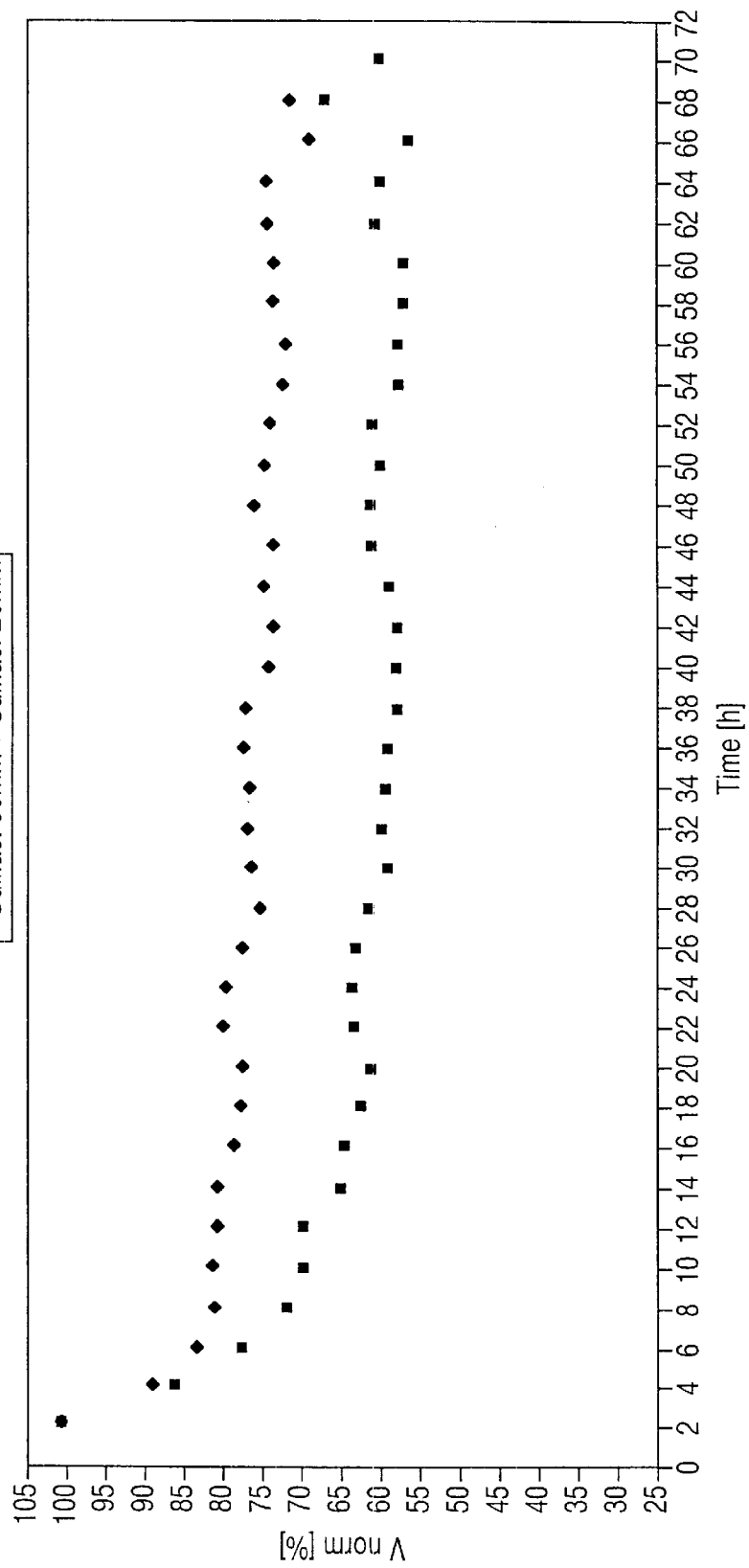
FIG. 9: Shows a graphical comparison of the normalized reaction rate for gas over time for two different electrolytic cells having copper electrodes and electrolyte compositions of: (1) 5.5 M $K_2HPO_4$ and 50 mM sulfamic acid; and (2) 5.5 M $K_2HPO_4$ and 20 mM sulfamic acid.

2. Use of the New Electrolyte in Cells Having a Controlled Variable Gas Delivery Rate Over a Period of Time The present invention also encompasses electrolytic cells which deliver gas at a controlled variable rate over a period of time. In such a cell, the rate of gas generation starts off high followed by a lower steady rate of gas generation. The rate of gas generation of this type of electrolytic cell is shown in FIGS. 6 and 9.

The rate of gas delivery depends upon: (1) the current flowing through the cell, and (2) the current efficiency of the particular gas evolution reaction, i.e., the presence or absence of side reactions. Thus, the rate of gas delivery can be controlled by choosing a combination of electrochemical reactions. The reactions can be chosen by changing the electrolyte, the electrode material, or both, as well as the resistor. A pump having controlled changes in drug delivery can be obtained by designing such an electrolytic cell.

For example, with the use of brass electrodes, zinc and copper provide anodic dissolution producing anode salt passivation, which occurs when the anode surface is coated and blocked by a salt film. This phenomenon, which occurs because of the low solubility of the zinc and copper phosphates, produces a sudden intensive increase in the cell potential and a corresponding decrease in current. Thus, following an initial high rate of gas production, the rate of gas delivery breaks and decreases, staying constant thereafter.

Following the occurrence of anode salt passivation, the cell potential will be high enough for water electrolysis, i.e., about 2 V. Water electrolysis starts but has a very low current efficiency because of significant side reactions on both electrodes: on the anode, zinc and copper are dissolving and oxygen is evolving, while on the cathode, copper is being deposited and hydrogen is evolving. This is in contrast to the initial period of operation of the cell, in which zinc and copper anodic dissolution occurs, while only a high rate of hydrogen evolution occurs at the cathode.

The length of the initial time period of a high rate of gas production prior to anode salt passivation depends upon the level of current used in the cell. Higher current produces a faster rate of phosphate production in the electrolyte, resulting in a faster onset of salt passivation and a consequent increase of cell potential. The theoretical limit of maximum time of cell operation is very prolonged.

3. Use of the New Electrolyte in Cells Having Pulsatile Current

Figure 10:
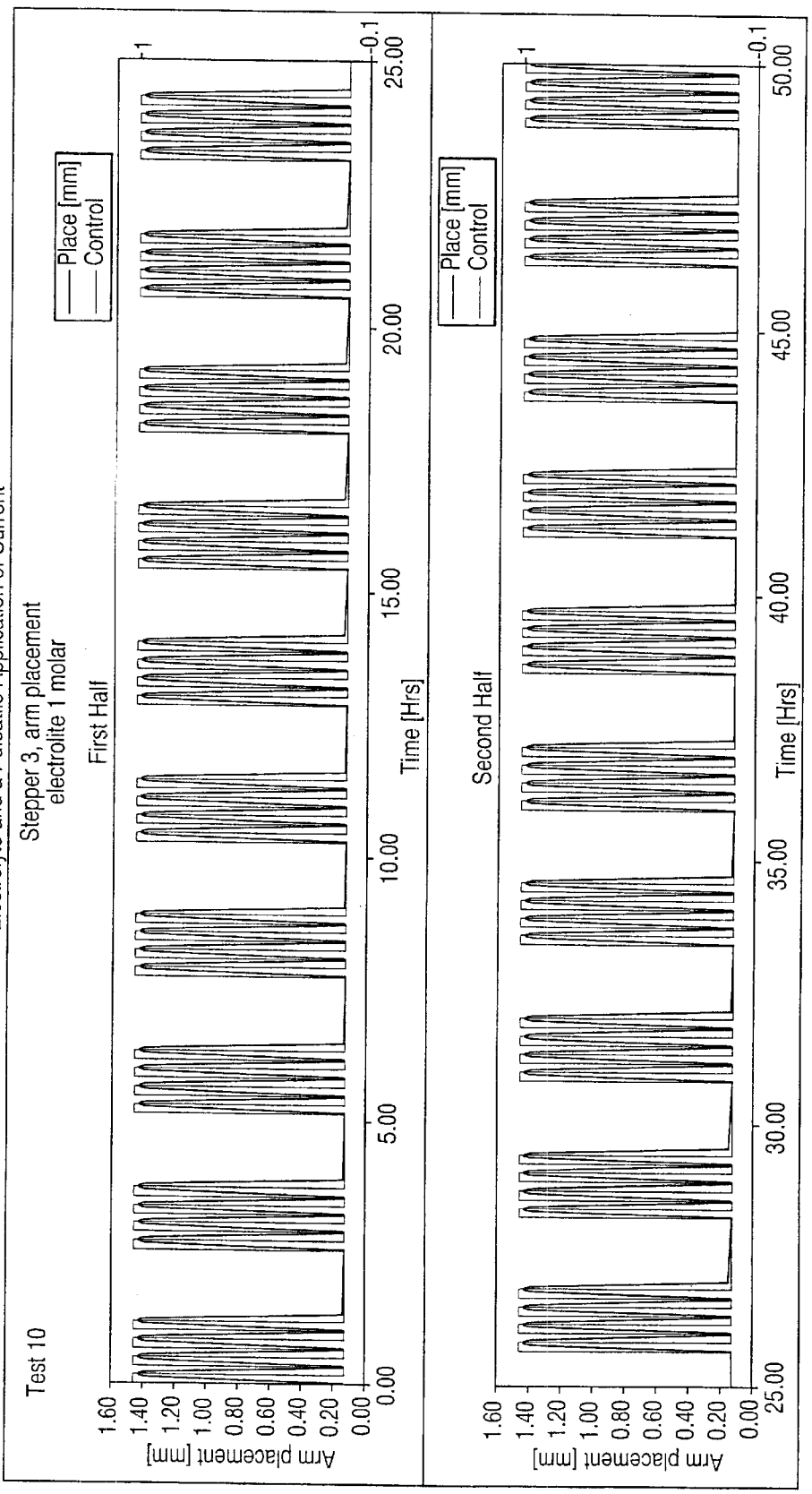
FIG. 10: Shows pulsatile gas delivery for an electrolytic cell having 1 M $K_2HPO_4$ as an electrolyte.
Figure 11:
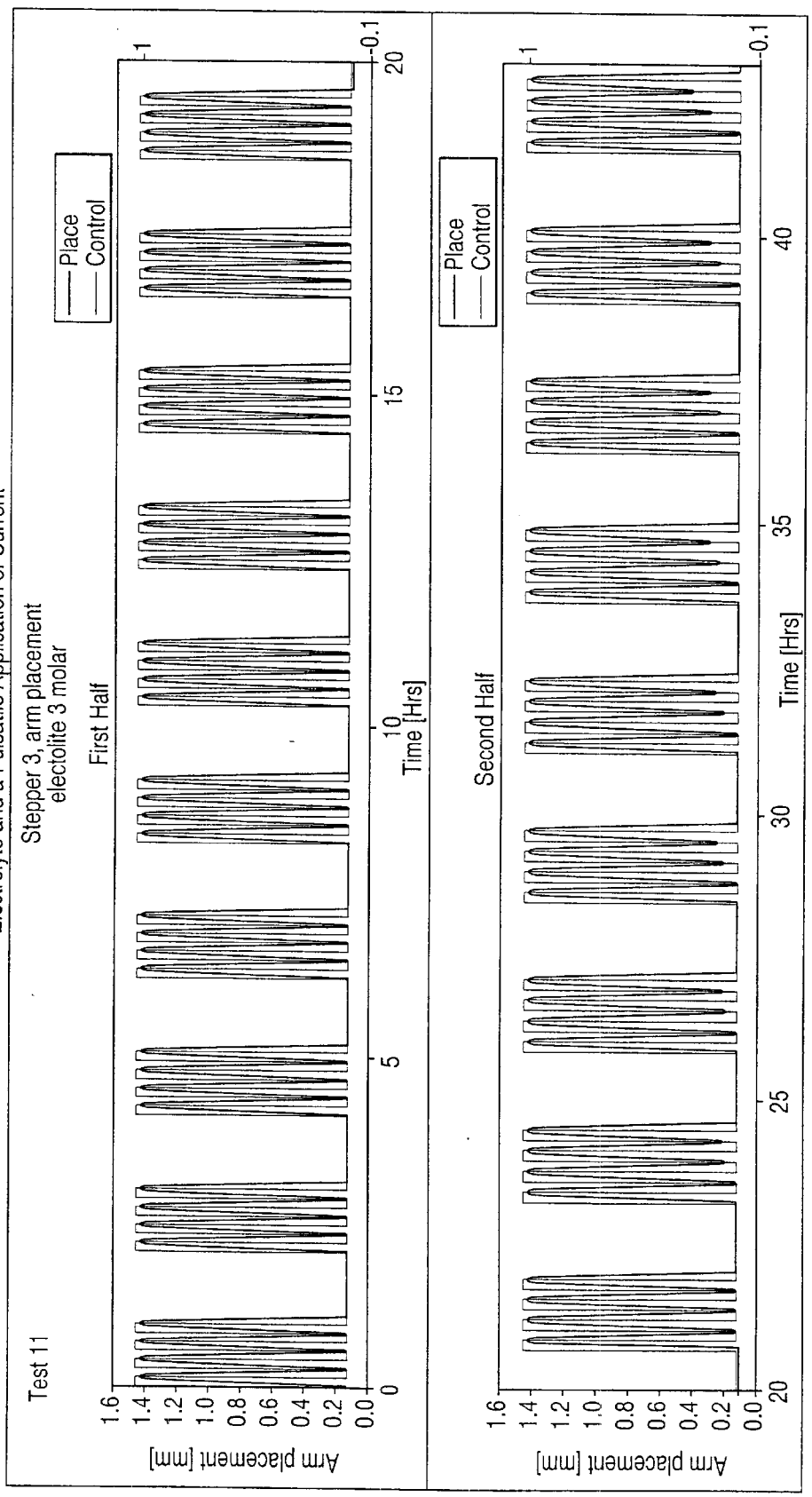
FIG. 11: Shows pulsatile gas delivery for an electrolytic cell having 3 M $K_2HPO_4$ as an electrolyte.

The present invention also encompasses electrolytic cells which deliver gas at a pulsatile rate over a period of time. In such a cell, the rate of gas generation starts and stops as the current starts and stops. The rate of gas generation of this type of electrolytic cell is shown in FIGS. 10 and 11.

The best performance of hormones, such as human growth hormone or fertility hormones, is obtained with pulsatile delivery rather than continuous delivery. (This is a characteristic of hormones.) A pulsatile insulin delivery device utilizing the electrolytic cell of the invention can be designed to delivery insulin at a specified time schedule, i.e., rate level I during the day and rate level II at night. The pulsatile delivery is obtained by starting and stopping the current run through the device. The time of starting and stopping can be triggered by a timing device incorporated into the delivery device.

E. Use of the New Electrolyte and/or Electrode Compositions in an Electrolytic Cell in a Drug Delivery Device The new electrolyte and/or the new electrodes can be used in electrolytic cells which function as gas generators for continuous or pulsatile drug delivery devices. For example, an electrolytic cell according to the invention can be used in a low-cost disposable device for single use. Such devices can be fixed to a band or strap for attachment to the body, e.g., the arm, of the person to receive the medicament dispensed from the device.

Such a device comprises a power supply for energizing the electrodes. The power supply preferably includes a battery and an electrical control circuit for controlling the rate of energization of the electrode, and thereby the rate of dispensing the liquid from the container. Such an electrical control circuit preferably includes presettable means for presetting the rate of energization of the electrodes, and an electrical switch for controlling the energization of the electrodes.

A miniaturized cell for use in the human body preferably has a minimum of ½ to 1 ml of electrolyte solution. Commercial size electrolyte cells can have 100's of liters of electrolyte solution. A typical miniaturized electrolytic cell for use in an external drug delivery device has a minimum of about 0.15 ml of electrolyte solution. The use of about 0.15 ml of electrolyte solution in a cell utilizing conventional electrodes resulted in a cell having a high potential. Therefore, electrolytic cells having quantities of electrolyte less than about 0.2 ml preferably employ special electrodes having a larger surface area than conventional electrodes. A miniaturized electrolytic cell having about 0.2 ml of electrolyte solution can produce gas for a period of over 200 hours, i.e., for a week or longer.

F. Electrode Pretreatment Method

The electrode pretreatment method of the invention is useful for electrodes to be used in electrolytic cells. The pretreatment produces cells having consistent and repeatable results. The electrodes can be made of, for example, stainless steel, copper, brass, or nickel.

For stainless steel electrodes: The electrodes are first washed in a solution of absolute or 95% ethyl alcohol. Preferably, the electrodes are washed in an ultrasonic bath in a closed glass vial for about 30 to about 40 minutes. This step removes fats and organic materials (dirt) from the electrode surface. The electrodes are then rinsed in deionized or RO (reverse osmosis) water.

This is followed by dipping the electrodes in a solution of about 5% citric acid in deionized or RO water. Preferably, the electrodes are dipped at 40–45° C. for about 30 to about 40 min. This step removes oxides or other remaining film from the electrodes. The electrodes are then rinsed in deionized or RO (reverse osmosis) water.

Finally, the electrodes are stored in the electrolyte solution ($K_2HPO_4$) for less than about 10 minutes to up to several days. The purpose of this step is to keep the electrode surface active and to prevent oxidation and contamination of the surface from exposure to the air.

For copper and brass electrodes: The process used for stainless steel electrodes is slightly modified for copper and brass electrodes. For copper electrodes, the dipping step was performed without the addition of heat and for a period of about 15 to about 20 minutes. For brass electrodes, the dipping step was performed without the addition of heat and for a period of about 5 to about 10 minutes.

For nickel electrodes: The washing and storage steps for nickel electrodes are the same as for stainless steel electrodes. The two processes differ in the dipping process. Pure nickel exposed to air has an oxide film on its surface (as does stainless steel). However, the nickel film is much more stable than that present on stainless steel.

Three alternative dipping solutions were developed for the nickel electrodes. The first solution comprises citric acid, ammonium acetate, and EDTA at an acidic pH. Preferably, the citric acid is present at about 0.5 M, the ammonium acetate is present at about 0.2 M, and the EDTA is added until dissolution.

The second dipping solution comprises citric acid, ethylenediamine, and a reducing agent, such as $NaHSO_3$. Preferably, the citric acid is present at a concentration of about 1 to about 2 M, the ethylenediamine is added until the pH remains acidic (pH of about 5), and the reducing agent is present at a concentration of about 0.01 M, depending upon the agent used.

The third dipping solution comprises ammonium nitrate, citric acid, triethanolamine, and a reducing agent, such as $NaHSO_3$ or sodium formaldehyde bisulfite. Preferably, the ammonium nitrate is present at a concentration of about 2.5 M, the citric acid is present at a concentration of about 0.01 M, the triethanolamine is present at a concentration of about 0.05 M, and the reducing agent is present at a concentration of about 0.01 M, depending upon the agent used.

The following examples are given to illustrate the present invention. It should be understood, however, that the invention is not to be limited to the specific conditions or details described in these examples. Throughout the specification, any and all references to a publicly available document, including U.S. patents, are specifically incorporated into this patent application by reference.

EXAMPLE 1

The purpose of this example was to demonstrate the rate of gas production of an electrolytic cell having a solution of $K_2HPO_4$ as an electrolyte.

Stainless steel electrodes (316 L) were used with a 5.5 M solution of $K_2HPO_4$ as an electrolyte in three electrolytic cells. The electrodes had a diameter of 0.8 mm, a length immersed in solution of 9 mm, for a total surface area of each electrode of 0.23 cm$^2$. 316 L stainless steel was used because it is highly resistant to corrosion. "L" represents low carbon concentration in the steel, which is preferable because of possible electrolyte contamination with "sludge". Sludge in electrochemistry refers to particles of anode falling into electrolyte due to un-uniform anodic corrosion. Low carbon content in the stainless steel minimizes the amount of insoluble sludge.

Figure 1:
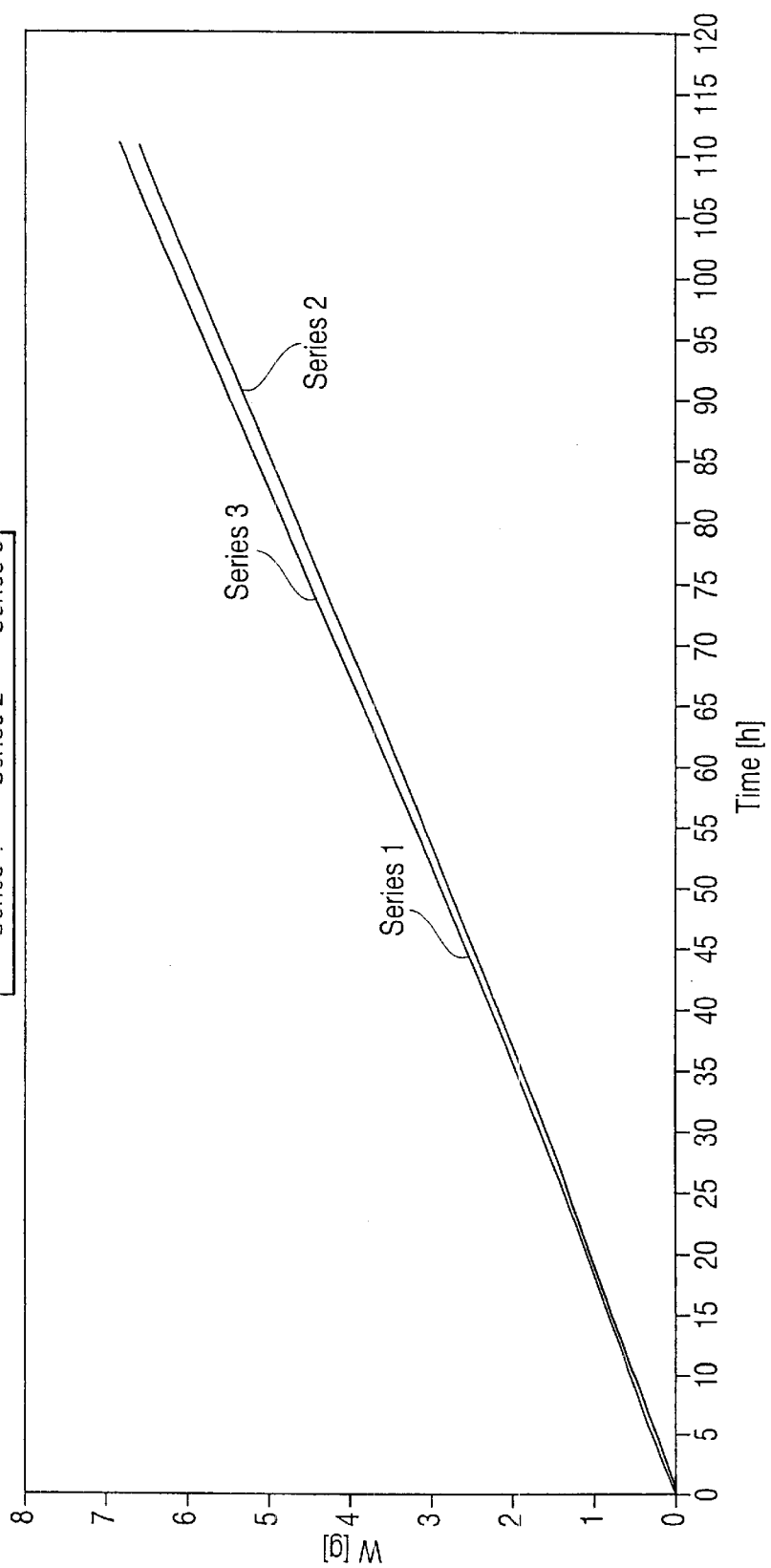
FIG. 1: Shows a graphical comparison of gas delivery over time for three different electrolytic cells having stainless steel electrodes and 5.5 M $K_2HPO_4$ as an electrolyte.
Figure 2:
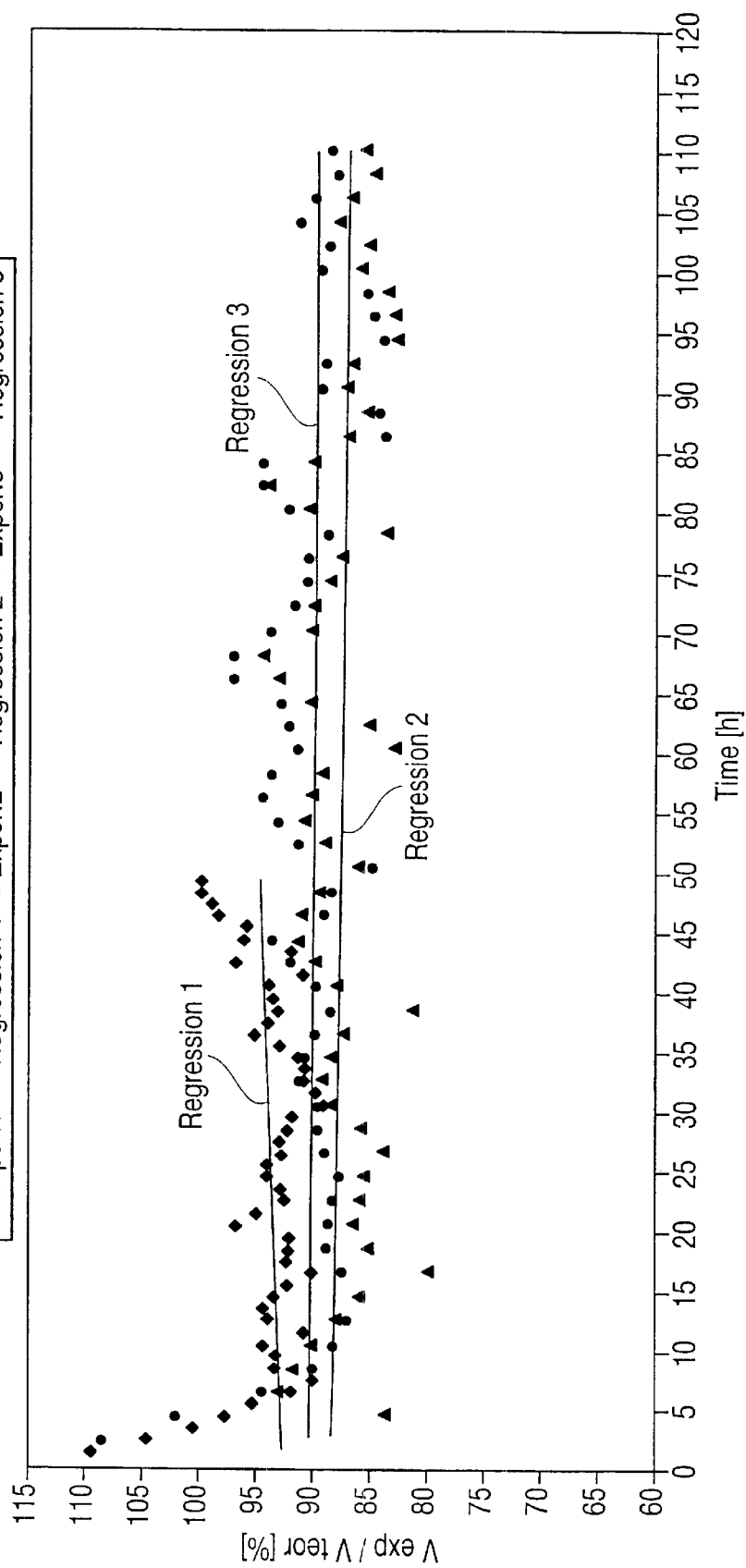
FIG. 2: Shows a graphical comparison of Faradaic current efficiency over time for three different electrolytic cells having stainless steel electrodes and 5.5 M $K_2HPO_4$ as an electrolyte.

The pH of the electrolyte used in each cell was 10.8. No additives were used with the electrolyte. The electrolytic cells generated gas at constant rates for a period of about 111 hours, with a Faradaic current efficiency of about 80 to about 100%. The resistance of the circuit was 10.2 kOhm. The constant rate of gas generation for over 4½ days for the three cells is shown in FIG. 1, and the current efficiency of the three cells is shown in FIG. 2.

The delivery rate for gas generation was measured as follows: evolving hydrogen and oxygen gas entered a water reservoir, pushing water via a tube into a vial on an analytical balance measuring continually on a time basis. The weight corresponded to the volume of gas generated (the y axis of FIG. 1).

The results of this example demonstrate the efficiency and effectiveness of $K_2HPO_4$ as an electrolyte for an electrolytic cell. Moreover, this example demonstrates the successful preparation of a simple, cost-effective, delivery device incorporating an electrolytic cell, in which the rate of gas generation is steady and constant over an extended period of time. This is significant as the rate of gas generation governs the rate of delivery of the substance contained in the device.

EXAMPLE 2

The purpose of this example was to construct an electrolytic cell that initially delivers a high rate of gas production followed by a lower steady rate of gas production.

Brass electrodes were used with a 5.5 M solution of $K_2HPO_4$ as an electrolyte in three electrolytic cells, having a pH of about 10.5 to about 11.0: Cell A, Cell B, and Cell C. EDTA (ethylenediaminetetra-acetic acid) was added to Cell B and sulfamic acid was added to Cell C. The composition of each of the three cells is summarized in Table 2 below.

TABLE 2

Compositions of Electrolytic Cells
Having Variable Rate of Gas Production

| Cell | Electrodes | Electrolyte | Additive |
|---|---|---|---|
| A | Brass | 5.5 M $K_2HPO_4$ | None |
| B | Brass | 5.5 M $K_2HPO_4$ | 20 mM EDTA |
| C | Brass | 5.5 M $K_2HPO_4$ | 50 mM sulfamic acid |

The results are summarized in FIGS. 3–6. The cell potential of the three cells was rather low, at 0.85 to 0.95 V and, therefore, current was rather high. See FIGS. 3 and 4. The resistance used was 10.9 kOhm. Initially, the delivery rate of hydrogen gas is high, as the current is initially high. In addition, the delivery rate of hydrogen gas is initially high as at the start of the reaction there is no side reaction on the cathode (where hydrogen gas evolves). This initial period of a high rate of gas production lasts for about 7 to about 11 hours. See e.g., FIG. 5, which shows the rate of delivery over time, including the break point, for the three cells.

Figure 3:
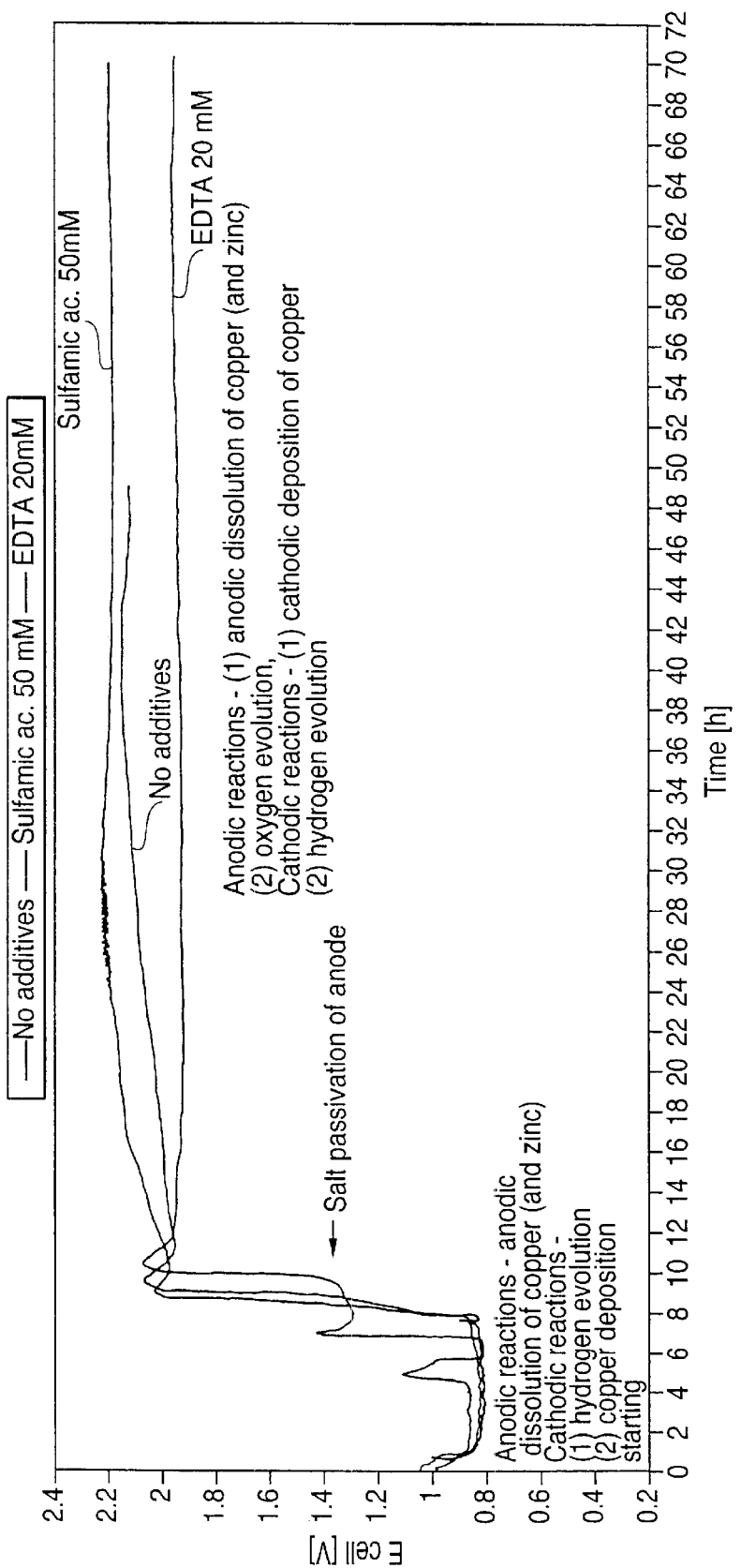
FIG. 3: Shows a graphical comparison of cell potential over time for three different electrolytic cells having brass electrodes and an electrolyte composition of: (1) 5.5 M $K_2HPO_4$; (2) 5.5 M $K_2HPO_4$ and EDTA; and (3) 5.5 M. $K_2HPO_4$ and sulfamic acid.
Figure 4:
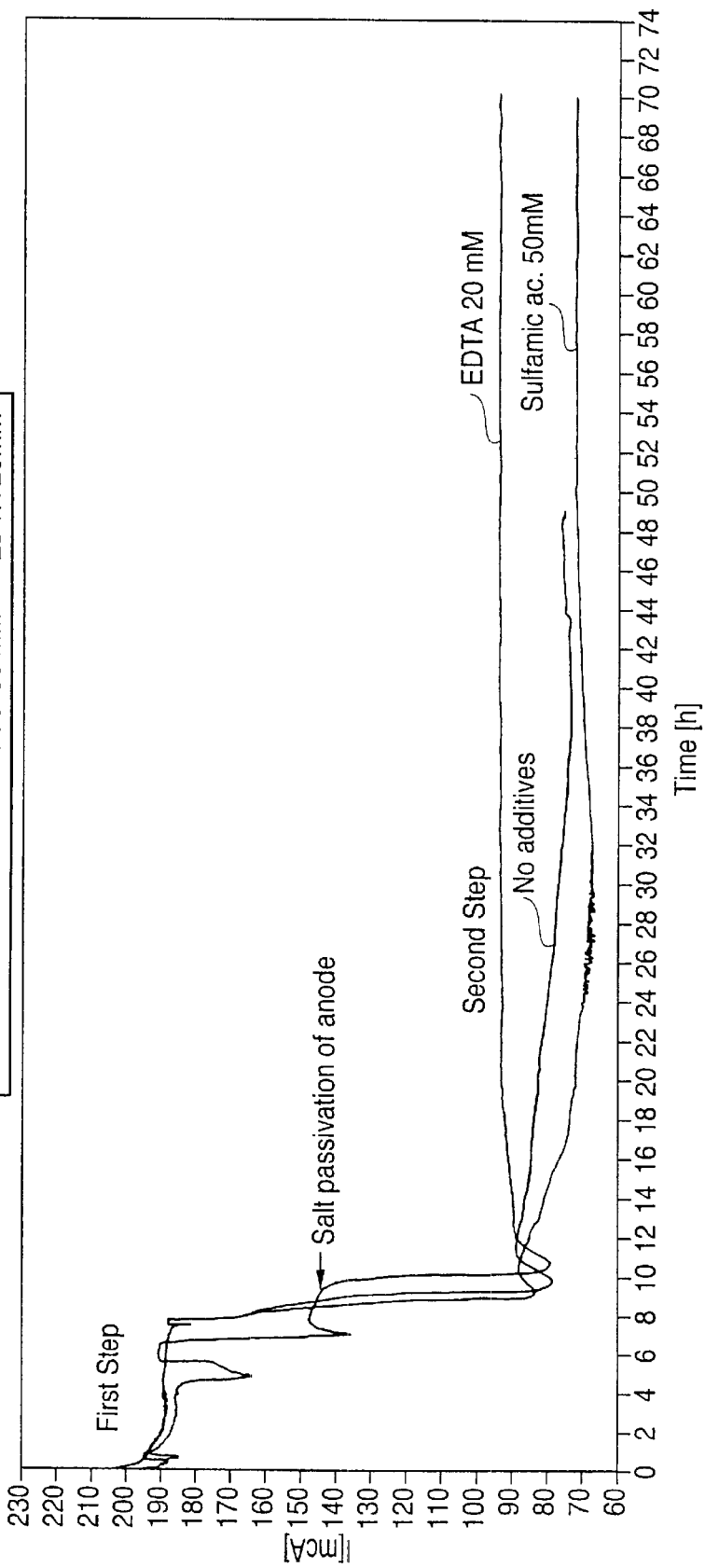
FIG. 4: Shows a graphical comparison of cell current over time for three different electrolytic cells having brass electrodes and electrolyte compositions of: (1) 5.5 M. $K_2HPO_4$; (2) 5.5 M. $K_2HPO_4$ and EDTA; and (3) 5.5 M. $K_2HPO_4$ and sulfamic acid.
Figure 5:
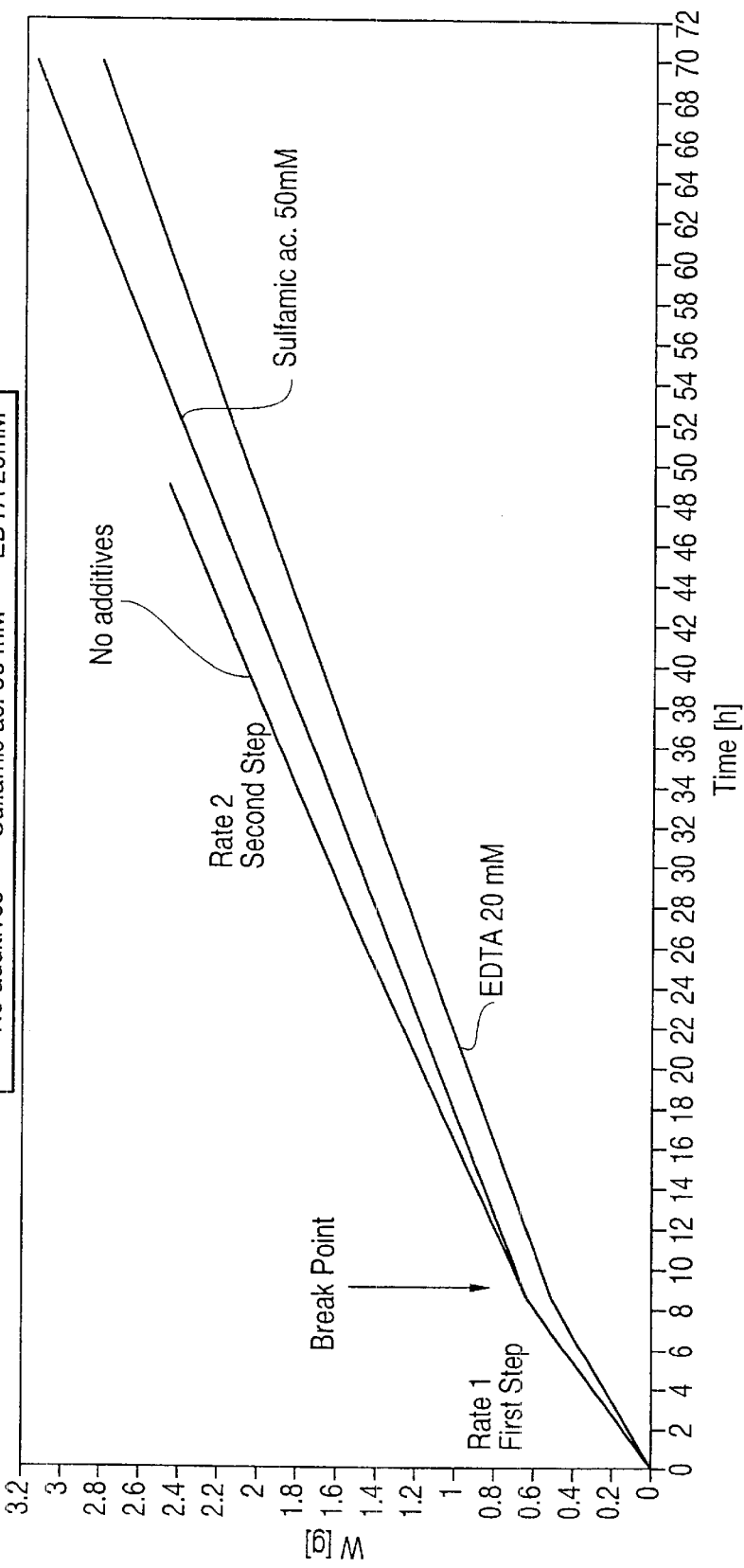
FIG. 5: Shows a graphical comparison of gas delivery over time by three different electrolytic cells having brass electrodes and electrolyte compositions of: (1) 5.5 M. $K_2HPO_4$; (2) 5.5 M. $K_2HPO_4$ and EDTA; and (3) 5.5 M. $K_2HPO_4$ and sulfamic acid.

As the reaction progresses, zinc and copper are gradually dissolved anodically, producing salt passivation of the anode and a sudden intensive increase in the cell potential along with a corresponding decrease in current. See e.g., FIG. 4. Once anodic salt passivation has occurs, the cell potential is high enough for water electrolysis, about 2 V. Water electrolysis starts but has a very low current efficiency because of significant side reactions on both electrodes: on the anode, zinc and copper are dissolving and oxygen is evolving; and on the cathode, copper is being deposited in addition to hydrogen evolving. As a result, the gas delivery curve breaks after about 7 to 11 hours, and the gas delivery rate decreases about 2 to 2.5 times, staying constant thereafter, as shown in FIG. 3.

This example demonstrates the successful preparation of a delivery device incorporating an electrolytic cell in which the rate of gas generation, which governs the rate of delivery of the substance contained in the device, is initially high followed by a lower steady rate of gas production.

EXAMPLE 3

The purpose of this example was to construct an electrolytic cell that initially delivers a high rate of gas production followed by a lower steady rate of gas production.

Copper electrodes were used with a 5.5 M solution of $K_2HPO_4$ as an electrolyte in five electrolytic cells, having a pH of about 10.5 to 11.0: Cell D, Cell E, Cell F, Cell G and Cell H. EDTA was added in varying amounts to three of the cells and sulfamic acid was added to the remaining two cells, as described in Table 3.

TABLE 3

Compositions of Electrolytic Cells Having Variable Rate of Gas Production

| Cell | Electrodes | Electrolyte | Additive |
|------|-----------|-------------|----------|
| D | Copper | 5.5 M $K_2HPO_4$ | 10 mM EDTA |
| E | Copper | 5.5 M $K_2HPO_4$ | 20 mM EDTA |
| F | Copper | 5.5 M $K_2HPO_4$ | 40 mM EDTA |
| G | Copper | 5.5 M $K_2HPO_4$ | 50 mM sulfamic acid |
| H | Copper | 5.5 M $K_2HPO_4$ | 20 mM sulfamic acid |

Figure 7:
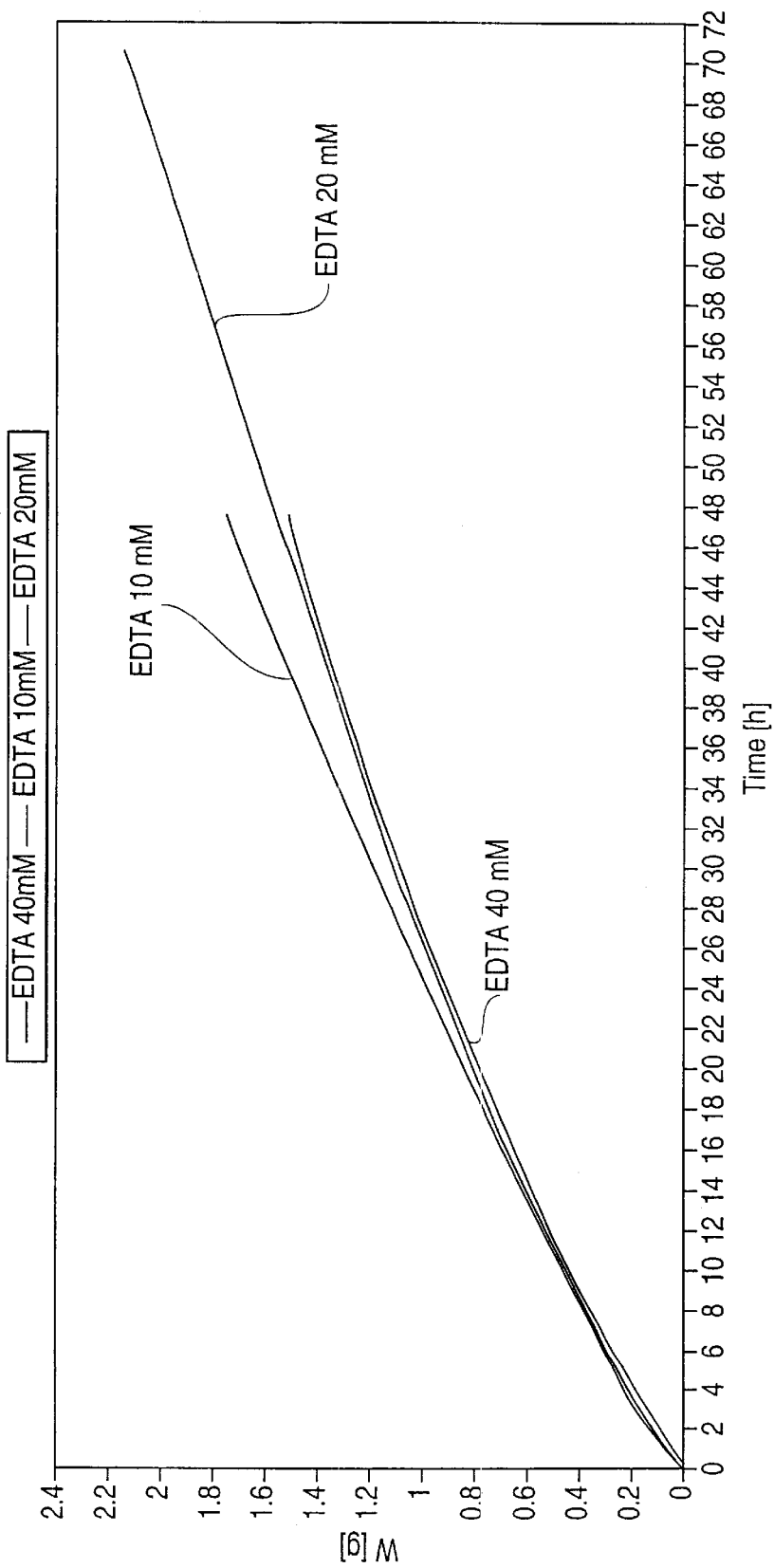
FIG. 7: Shows a graphical comparison of gas delivery over time for three different electrolytic cells having copper electrodes and electrolyte compositions of: (1) 5.5 M $K_2HPO_4$ and 40 mM EDTA; (2) 5.5 M $K_2HPO_4$ and 20 mM EDTA; and (3) 5.5 M $K_2HPO_4$ and 10 mM EDTA.
Figure 8:
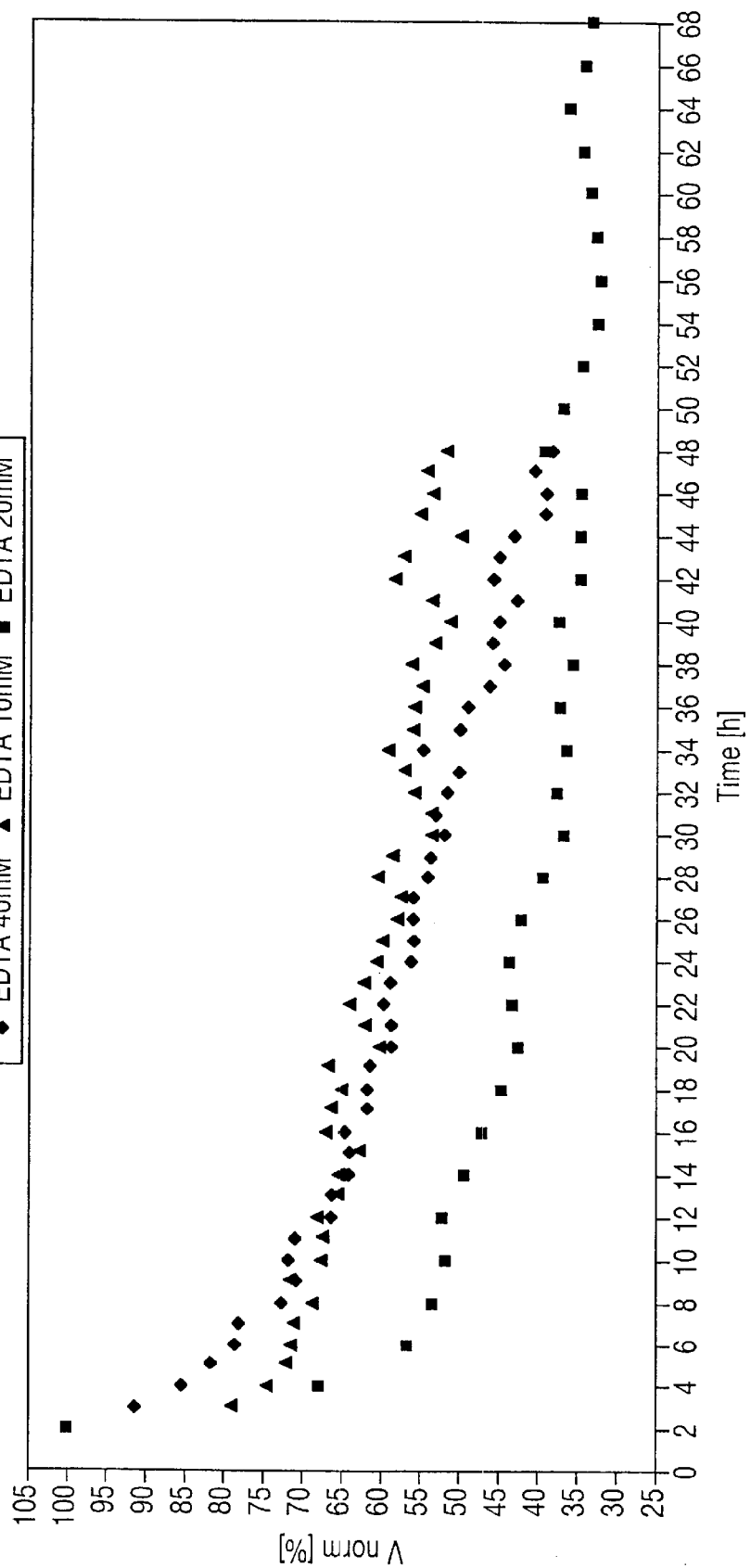
FIG. 8: Shows a graphical comparison of the normalized reaction rate for gas over time for three different electrolytic cells having copper electrodes and electrolyte compositions of: (1) 5.5 M $K_2HPO_4$ and 40 mM EDTA; (2) 5.5 M $K_2HPO_4$ and 20 mM EDTA; and (3) 5.5 M $K_2HPO_4$ and 10 mM EDTA.

The results are summarized in FIG. 7, which shows the rate of delivery over time for the three EDTA cells; and FIGS. 8 and 9, which show the normalized reaction rate over time for the three EDTA cells and the sulfamic acid cells, respectively.

There are two primary differences between a cell having brass electrodes (Example 2) and a cell having copper electrodes. First, there is no break point in the delivery curve because salt passivation does not occur with copper electrodes. Second, water electrolysis starts immediately.

A. Lack of Salt Passivation with Copper Electrodes

With the use of brass electrodes, zinc apparently acts as a reducing agent resulting in copper and zinc phosphate formation (with and without additives in the electrolyte). The phosphate salts are significantly insoluble, resulting in salt passivation of the anode.

In contrast, copper electrode cells having EDTA or sulfamic acid as additives, oxygen evolution and anodic dissolution of copper until it complexes occurs at the anode, and hydrogen evolution and electrodeposition of copper from complexes occurs at the cathode. For a cell lacking EDTA or sulfamic acid as additives, oxygen evolution and anodic dissolution of copper until CuO (black powder) formation occurs at the anode, and hydrogen evolution occurs at the cathode.

Cells having copper electrodes and EDTA or sulfamic acid as an additive have increased anodic dissolution of copper, creating soluble copper complexes. This enables an additional cathodic reaction of electrodeposition of copper from the created complexes. The current fraction for both side reactions increases at first followed by reaching a steady state after a period of time.

Thus, the delivery rate curve for the copper electrode cells of this example is smooth, with no break point. In addition, the main reaction rate is slightly decreasing until it reaches a constant value. The decrease of gas evolution rate can be regulated with the addition of additives.

B. Immediate Water Electrolysis

The second primary difference between cells having brass and copper electrodes is that with copper electrodes the cell potential is high enough at the beginning of cell operation to effect water electrolysis (about 2 V). This is because copper anodes do not contain zinc.

Anodic dissolution of zinc occurs at significantly lower anodic potential than anodic dissolution of copper or oxygen evolution. The anodic dissolution of zinc, which occurs with brass electrodes (followed by anodic dissolution of copper), leads to an initial cell potential of less than 0.95 V, which is too low for water electrolysis.

This example demonstrates the successful preparation of a delivery device incorporating an electrolytic cell in which the rate of gas generation, which governs the rate of delivery of the substance contained in the device, is initially high followed by a lower steady rate of gas production.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. An electrolytic cell comprising:
   (a) an electrolyte solution comprising K2HPO4, or a less alkaline phosphate buffer solution, in water, said electrolyte being present at a concentration of about 1 to about 6 M and in an amount of from about 0.15 ml to about 100 L;
   (b) at least two electrodes comprising an anode and a cathode, wherein:
      (i) said anode and cathode comprise stainless steel and have a surface area of about 0.19 $cm^2$ to about 50 $cm^2$ or more;
      (ii) the electrodes are connectable to a source of electrical current, wherein the electrodes are energized by an electrical current that is less than or equal to about 2 mA, said current being conducted through the electrolyte resulting in a gas forming at each electrode, said gas being generated at a steady rate or at a pulsatile rate and is produced at a rate of from about 0.01 ml of gas/hr up to about 1.5 ml of gas/hour.

2. The electrolytic cell of claim 1 comprising means for dispensing a liquid at a predetermined.

3. An electrolytic cell comprising:
   (a) an electrolyte solution comprising K2HPO4, or a less alkaline phosphate buffer solution, in water, said electrolyte being present at a concentration of about 1 to about 3 M and in an amount of from about 0.2 ml to about 100 L;
   (b) at least two electrodes comprising an anode and a cathode, wherein:
      (i) said anode and cathode comprise stainless steel and have a surface area of about 0.19 $cm^2$ to about 50 $cm^2$ or more;
      (ii) the electrodes are connectable to a source of electrical current, wherein the electrodes are energized by an electrical current that is about 7 mA or greater, said current being conducted through said electrolyte resulting in a gas forming at each electrode, said gas being generated at a steady rate or at a pulsatile rate and is produced at a rate of at least 4 ml gas/hour.

4. The electrolytic cell of claim 3 comprising means for dispensing a liquid at a predetermined.

5. An electrolytic cell comprising:
   (a) an electrolyte solution comprising $K_2HPO_4$, or a less alkaline phosphate buffer solution, in water, and wherein the electrolyte is present at a concentration of about 1 to about 6 M and in an amount of from about 0.15 ml. to about 100 L;

(b) at least two electrodes comprising an anode and a cathode, wherein:
  (i) the electrodes are made of a conductive material;
  (ii) the anode is electrochemically soluble and the anode comprises copper or brass;
  (iii) the electrodes have a surface area of about 0.19 cm$^2$ to about 50 cm$^2$ and are connectable to a source of electrical current wherein the current is less than or equal to about 2 mA; and,
  wherein when the electrodes are energized by an electrical current, the current is conducted through the electrolyte resulting in a gas forming at one or more of the electrodes, said gas being generated at a rate of from about 0.001 ml of gas/hr up to about 1.5 ml of gas/hour.

6. The electrolytic cell of claim 5 comprising means for dispensing a liquid at predetermined rate.

7. An electrolytic cell comprising:

(a) an electrolyte solution comprising $K_2HPO_4$, or a less alkaline phosphate buffer solution, in water, and wherein the electrolyte is present at a concentration of about 1 to about 3 M and in an amount of from about 0.2 ml. to about 100 L;

(b) at least two electrodes comprising an anode and a cathode, wherein:
  (i) the electrodes are made of a conductive material;
  (ii) the anode is electrochemically soluble and the anode comprises copper or brass;
  (iii) the electrodes have a surface area of about 0.19 cm$^2$ to about 50 cm$^2$ and are connectable to a source of electrical current wherein the current is about 7 mA or greater;

and, wherein when the electrodes are energized by an electrical current, the current is conducted through the electrolyte resulting in a gas forming at one or more of the electrodes, said gas being generated at a rate of from about 0.01 ml of gas/hr up to about 24 ml of gas/hour.

8. The electrolytic cell of claim 7 comprising means for dispensing a liquid at a predetermined rate.

* * * * *

UNITED STATES PATENT AND TRADEMARK OFFICE
CERTIFICATE OF CORRECTION

PATENT NO. : 6,572,740 B2
DATED : June 3, 2003
INVENTOR(S) : Rosenblum et al.

It is certified that error appears in the above-identified patent and that said Letters Patent is hereby corrected as shown below:

Column 18,
Lines 44 and 64, after the word "predetermined" insert the word -- rate --.

Signed and Sealed this

Thirtieth Day of December, 2003

JAMES E. ROGAN
*Director of the United States Patent and Trademark Office*